(12) United States Patent
Chappuis

(10) Patent No.: US 8,728,132 B2
(45) Date of Patent: May 20, 2014

(54) INTERNAL PEDICLE INSULATOR APPARATUS AND METHOD OF USE

(76) Inventor: James L. Chappuis, Marietta, GA (US)

( * ) Notice: Subject to any disclaimer, the term of this patent is extended or adjusted under 35 U.S.C. 154(b) by 1925 days.

(21) Appl. No.: 11/712,257

(22) Filed: Feb. 28, 2007

(65) Prior Publication Data

US 2007/0162027 A1 Jul. 12, 2007

Related U.S. Application Data

(63) Continuation-in-part of application No. 11/110,005, filed on Apr. 20, 2005, now Pat. No. 7,338,500.

(60) Provisional application No. 60/563,797, filed on Apr. 20, 2004.

(51) Int. Cl.
*A61B 17/58* (2006.01)
*A61B 17/70* (2006.01)
*A61B 17/84* (2006.01)

(52) U.S. Cl.
USPC ............. 606/300; 606/86 A; 606/92; 606/246

(58) Field of Classification Search
USPC .............. 606/92, 99, 104, 279, 304, 76, 300, 606/302, 322
See application file for complete search history.

(56) References Cited

U.S. PATENT DOCUMENTS

| | | | | |
|---|---|---|---|---|
| 4,653,489 | A * | 3/1987 | Tronzo | 606/65 |
| 5,562,736 | A * | 10/1996 | Ray et al. | 606/86 A |
| 6,048,343 | A * | 4/2000 | Mathis et al. | 606/916 |
| 6,093,207 | A | 7/2000 | Pisharodi | |
| 6,214,012 | B1 * | 4/2001 | Karpman et al. | 606/93 |
| 6,306,156 | B1 | 10/2001 | Clark | |
| 2003/0065329 | A1 * | 4/2003 | Vaughan | 606/61 |
| 2004/0267277 | A1 * | 12/2004 | Zannis et al. | 606/99 |
| 2005/0055026 | A1 * | 3/2005 | Biedermann et al. | 606/73 |
| 2005/0085813 | A1 * | 4/2005 | Spitler et al. | 606/61 |

* cited by examiner

*Primary Examiner* — Christian Sevilla
(74) *Attorney, Agent, or Firm* — McHale & Slavin, P.A.

(57) ABSTRACT

Internal pedicle insulator apparatuses and methods are provided. A representative method includes: providing an internal pedicle insulator implant; inserting the implant into a pedicle such that the implant is positioned between a nerve and material that is to be applied in a vicinity of the nerve; applying the material in the vicinity of the nerve; and using the implant to prevent the material from contacting the nerve.

7 Claims, 2 Drawing Sheets

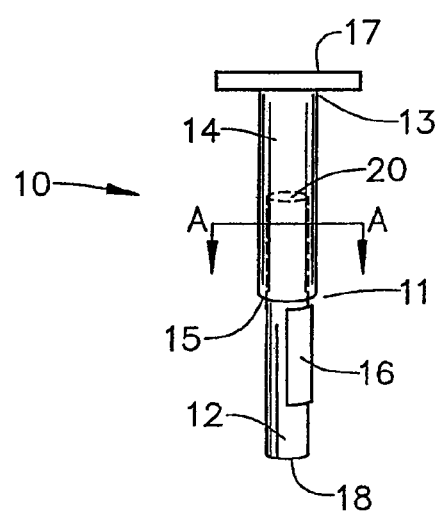
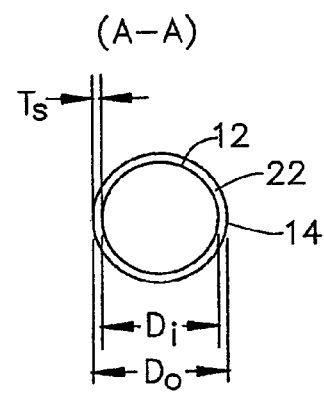
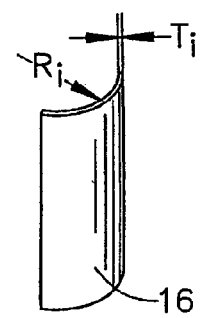
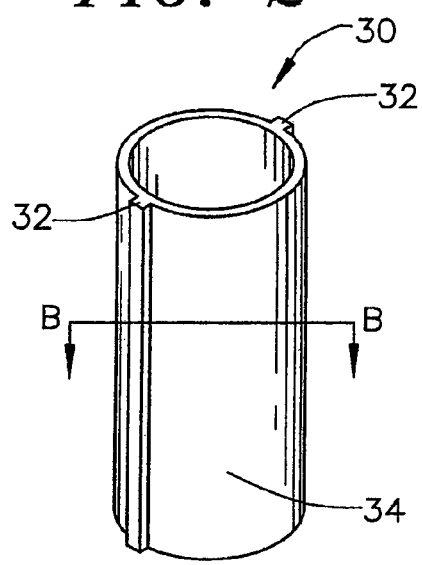
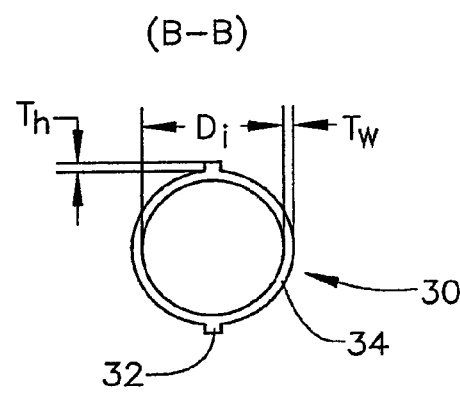

FIG. 3
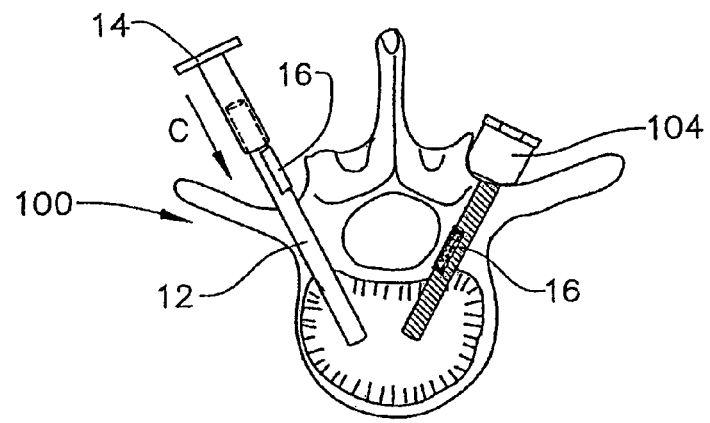
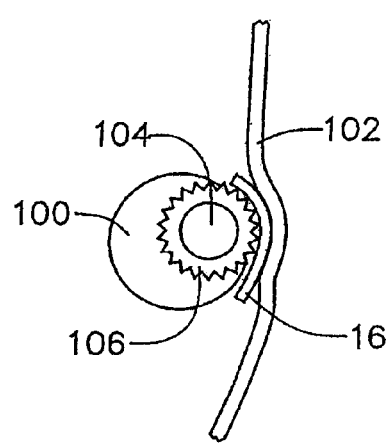
FIG. 4
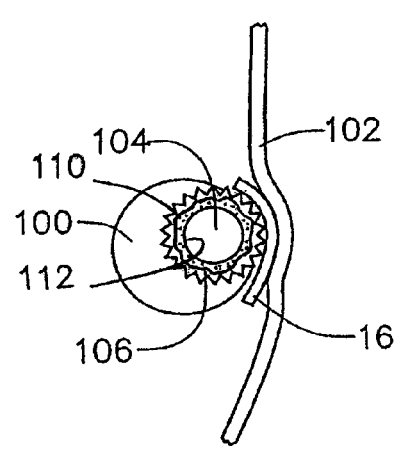
FIG. 5

INTERNAL PEDICLE INSULATOR APPARATUS AND METHOD OF USE

CROSS-REFERENCE TO RELATED APPLICATIONS

This application is a Continuation-in-Part application, which claims priority to U.S. patent application entitled, "Internal Pedicle Insulator Apparatus and Method of Use," having Ser. No. 11/110,005 filed on Apr. 20, 2005, now U.S. Pat. No. 7,338,500, which claims priority to U.S. provisional application entitled, "Internal Pedicle Insulator Apparatus" having Ser. No. 60/563,797 filed on Apr. 20, 2004, both of which are entirely incorporated herein by reference.

FIELD OF THE INVENTION

The present invention generally relates to surgical instruments and tools, and in particular, relates to an internal pedicle insulator apparatus.

BACKGROUND OF THE INVENTION

The human spine is composed of a column of thirty-three bones, called vertebra, and their adjoining structures. The twenty-four vertebrae nearest the head are separate bones capable of individual movement and are generally connected by anterior and posterior longitudinal ligaments and by discs of fibrocartilage, called intervetebral discs, positioned between opposing faces of adjacent vertebrae. The twenty-four vertebrae are commonly referenced in three sections. The cervical spine, closest to the head and often referenced as the "neck," comprises the first seven vertebrae of the spine. The thoracic spine and the lumbar spine are below the cervical spine. Each of the vertebra include a vertebral body and a dorsal arch, which enclose an opening, called the vertebral foramen, through which the spinal cord and the spinal nerve pass. The remaining nine vertebrae below the lumbar spine are fused to form the sacrum and the coccyx and are incapable of individual movement.

Degeneration of the lumbar spine can be cause the human spine is composed of a column of thirty-three bones, called vertebra, and their adjoining structures. The twenty-four vertebrae nearest the head are separate bones capable of individual movement and are generally connected by anterior and posterior longitudinal ligaments and by discs of fibrocartilage, called intervetebral discs, positioned between opposing faces of adjacent vertebrae. The twenty-four vertebrae are commonly referenced in three sections. The cervical spine, closest to the head and often referenced as the "neck," comprises the first seven vertebrae of the spine. The thoracic spine and the lumbar spine are below the cervical spine. Each of the vertebra include a vertebral body and a dorsal arch, which enclose an opening, called the vertebral foramen, through which the spinal cord and the spinal nerve pass. The remaining nine vertebrae below the lumbar spine are fused to form the sacrum and the coccyx and are incapable of individual movement.

The degeneration of any portion of the lumbar spine can result in instability of the spine, which can lead to impingement or damage to the spinal cord or nerve roots. Impingement of the spinal column or nerve root can result in pain. Damage to spinal cord or nerve roots can result in reduced motor skills or even paralysis. Degeneration of the lumbar spine can be a result of fractures, tumors or other various degenerative diseases.

It is well known that utilization of pedicle screws for posterior lumbar stabilization procedures. These procedures typically include inserting a pedicle screw posteriorly into the pedicle or pillar of the lumbar spine. The screw is then connected to plates or rods for stabilization of the lumbar spine. A bone graft also can be added to help solidify the stabilization. The pedicle screw may be inserted off center, such as, for example, too medial, which may impinge on the associated nerve root causing pain. This requires a repositioning of the screw. However, even after repositioning there may be an effect on the pedicle wall, which can still cause nerve root irritation. Such procedures are also susceptible to loosening of the screw.

Thus, a heretofore unaddressed need exists in the industry to address the aforementioned deficiencies and inadequacies.

SUMMARY OF THE INVENTION

Internal pedicle insulator apparatuses and methods are provided. An exemplary embodiment of such a method comprises: providing an internal pedicle insulator implant; inserting the implant into a pedicle such that the implant is positioned between a nerve and material that is to be applied in a vicinity of the nerve; applying the material in the vicinity of the nerve; and using the implant to prevent the material from contacting the nerve.

An exemplary embodiment of an internal pedicle insulator apparatus, comprises: an inner insertion rod having a top end and an opposing bottom end; an outer insertion rod having an upper end and a lower end, the outer insertion rod being arranged and configured to substantially correspond to the inner insertion rod; and an internal pedicle insulator implant. The inner insertion rod is arranged and configured to be slidably engaged inside the outer insertion rod, and the inner insertion rod and the outer insertion rod are arranged and configured to position the internal pedicle insulator implant such that material applied in a vicinity of a nerve located in a pedicle is prevented from irritating the nerve by being mechanically blocked by the internal pedicle insulator implant.

Another exemplary embodiment of an internal pedicle insulator apparatus, comprises: an inner insertion rod having a top end and an opposing bottom end; an outer insertion rod having an upper end and an opposing lower end; and an internal pedicle insulator implant. The inner insertion rod and the outer insertion rod are arranged and configured to insert and position the internal pedicle insulator implant such that cement used to secure a pedicle screw does not irritate a nerve located in a vicinity of the cement.

Other systems, methods, features, and advantages of the present invention will be or become apparent to one with skill in the art upon examination of the following drawings and detailed description. It is intended that all such additional systems, methods, features, and advantages be included within this description, be within the scope of the present invention, and be protected by the accompanying claims.

BRIEF DESCRIPTION OF THE DRAWINGS

The invention can be better understood with reference to the following drawings. The components in the drawings are not necessarily to scale, emphasis instead being placed upon clearly illustrating the principles of the present invention. Moreover, in the drawings, like reference numerals designate corresponding parts throughout the several views.

FIG. 1 is a side view of an embodiment of the internal pedicle insulator apparatus of the present invention.

FIG. 1A is a cross-sectional top view of an embodiment of the internal pedicle insulator apparatus illustrated in FIG. 1.

FIG. 1B is a perspective view of an embodiment of an internal pedicle insulator implant of the internal pedicle insulator apparatus illustrated in FIG. 1.

FIG. 2 is a perspective view of an embodiment of an internal pedicle insulator implant of the internal pedicle insulator apparatus illustrated in FIG. 1.

FIG. 2A is a cross-sectional top view of an embodiment of an internal pedicle insulator implant illustrated in FIG. 2.

FIG. 3 is a side view of the internal pedicle insulator apparatus illustrated in FIG. 1 in use.

FIG. 4 is a top view of the internal pedicle insulator implant of the internal pedicle insulator apparatus illustrated in FIG. 1 in use.

FIG. 5 is a top view of another embodiment of an internal pedicle insulator implant of the internal pedicle insulator apparatus in use.

DETAILED DESCRIPTION OF THE PREFERRED EMBODIMENTS

FIG. 1 illustrates one preferred embodiment of an internal pedicle insulator apparatus 10. The internal pedicle insulator apparatus 10 comprises an inner insertion rod 12, an outer insertion rod 14, and an internal pedicle insulator implant 16.

The inner insertion rod 12 has a bottom end 18 and an opposing top end 20. It is preferable that the inner insertion rod 12 has a substantially round cross-section. However, it should be noted that the inner insertion rod 12 can comprise any suitable configuration. The inner insertion rod 12 can comprise any suitable material, such as titanium, as merely one example.

The outer insertion rod 14 has a lower end 11 and an opposing upper end 13. An opening 15 is disposed at the lower end 11. An optional handle 17 can be disposed toward the upper end 13 of the outer insertion rod 14 to facilitate use of the internal pedicle insulator apparatus 10. An opening at the upper end 13 of the outer insertion rod 14 through which the inner insertion rod 12 can pass can also be included (not shown). It is preferable that the outer insertion rod 14 has a substantially round cross-section. It should be noted, however, that the outer insertion rod 14 can comprise any suitable cross-section. The outer insertion rod 14 can comprise titanium, however, it should be understood that the outer insertion rod 14 can comprise any suitable material.

The outer insertion rod 14 is arranged and configured to receive the inner insertion rod 12 through the opening 15 disposed at the lower end 11 of the outer insertion rod 14. The inner insertion rod 12 is preferably slidably inserted into the outer insertion rod 14 such that the upper end 13 of the outer insertion rod 12 substantially corresponds to the top end 20 of the inner insertion rod 12. Similarly, the lower end 11 of the outer insertion rod 14 substantially corresponds with the bottom end 18 of the inner insertion rod 12. The inner insertion rod 12 is laterally slidable within the outer insertion rod 14.

Referring next to FIG. 1A, in one embodiment it is preferable that the outer insertion rod 14 is defined by a diameter $D_o$. The inner insertion rod 12 is defined by a diameter $D_i$. It is preferable that $D_o$ is greater than $D_i$ to facilitate the inner insertion rod 12 being slidably disposed within the outer insertion rod 14. It is further preferable that $D_o$ is less than $D_i$ such as to leave a space 22 having a thickness $T_s$ when the inner insertion rod 16 is disposed within the outer insertion rod 14.

As shown in FIG. 1B, in one embodiment the internal pedicle insulator implant 16 is substantially rectangular in shape and curved. It should be understood, however, that the internal pedicle insulator implant 16 can comprise any suitable shape and configuration. In this embodiment it is preferable that the internal pedicle insulator implant 16 is curved as defined by a radius $R_i$. It is preferable that the radius $R_i$ of the internal pedicle insulator implant 16 substantially corresponds to a pedicle screw 104 with which the internal pedicle insulator implant 16 is to be used. The internal pedicle insulator implant 16 is also defined by a thickness $T_i$. It is preferable that the thickness $T_i$ is greater than the thickness $T_s$ of space 22. The internal pedicle insulator implant 16 preferably comprises Poly Ether Ether-Ketone, but can comprise any suitable material.

FIGS. 2 and 2A illustrate another embodiment of an internal pedicle insulator implant 30. The internal pedicle insulator implant 30 is substantially tubular in shape and comprises a wall 34. The internal pedicle insulator implant 30 has a substantially circular cross-section, defined by a diameter $D_i$. The diameter $D_i$ is preferably arranged and configured to substantially correspond to a pedicle screw 104 with which the internal pedicle insulator implant 30 is to be used. Although a substantially circular cross-section is illustrated, it should be understood that the internal pedicle insulator can have any desired cross-sectional shape.

The internal pedicle insulator 30 optionally comprises at least one anti-rotation fin 32 extending outward from the wall 34. The anti-rotation fins 32 can extend the length of the wall 34 of internal pedicle insulator 30 or only a portion of the length. The anti-rotation fins 32 can comprise any configuration that discourage rotation of the internal pedicle insulator 30 when disposed in a desired position. In one embodiment, a thickness $T_w$ of the wall 34 of the internal pedicle insulator implant 30 in addition to a height $T_h$ of an anti-rotation fin 32 extending from the wall 34 is greater than thickness $T_s$ of the space 22 between the inner insertion rod 12 and the outer rotation rod 14 when the inner insertion rod 12 is disposed within the outer rotation rod 14.

In another embodiment the internal pedicle insulator implant 30 includes no anti-rotation fin 32 (not shown). In this embodiment, it is preferable that a thickness $T_w$ of a wall of the internal pedicle insulator implant 30 is greater than the thickness $T_s$ of the space 22 formed by the inner insertion rod 12 and the outer insertion rod 14 when the inner insertion rod 12 is disposed inside the outer insertion rod 14.

FIG. 3 illustrates the internal pedicle insulator apparatus 10 in use. A pedicle screw with which the internal pedicle insulator implant 16 is to be used is first removed from its position within the vertebral body. The inner insertion rod 12 is positioned as desired in the vertebral body 100, such as in a channel created by the pedicle screw 104. The internal pedicle insulator implant 16 is positioned adjacent the inner insertion rod 12. The outer insertion rod 14 is positioned around the inner insertion rod 12 via the opening 15 disposed at the lower end 11 of the outer insertion rod 14. The outer insertion rod 14 is moved in direction C toward the bottom end 18 of the inner insertion rod 12. As the outer insertion rod 14 is moved in direction C, the outer insertion rod 14 is moved toward the internal pedicle insulator implant 16 until the outer insertion rod 14 engages the internal pedicle insulator 16. Pressure is applied to the outer insertion rod 14 in direction C to slide the internal pedicle insulator 16 along the inner insertion rod 12 toward the vertebral body 100 until the internal pedicle insulator 16 is appropriately positioned within the vertebral body 100. The internal pedicle insulator implant 16 is held in position by friction applied to its curved configuration when properly inserted into position. After the internal pedicle insulator implant 16 is disposed in a desired position, the pedicle screw 104 is returned to its position within the vertebral body.

FIG. 4 illustrates one embodiment of an internal pedicle insulator implant 16 in a desired position. As shown, the internal pedicle insulator implant 16 is positioned between an affected nerve root 102 and a jagged hole 106 in the vertebral body 100 resulting from a compromised pedicle screw 104.

FIG. 5 illustrates another embodiment of an internal pedicle insulator implant 16. In this example, however, the implant is located to prevent cement, e.g., PMMA, from contacting the nerve root 102. Notably, the cement 110 is provided to anchor the pedicle screw 104. In other embodiments, various other types of materials can be prevented from contacting a nerve by using an implant. Such a material can be an injectable biological substance, for example.

Although cement can be provided externally with respect to the screw, the embodiment of FIG. 5 involves a screw that incorporates holes or fenestrations e.g., fenestration 112. As such, the cement can be injected into the screw and then a portion of that cement can be pass through the fenestrations and into the surrounding tissue. Thus, the implant 16 serves as a physical barrier to prevent the cement from impinging upon the nerve root.

It should be emphasized that the above-described embodiments of the present invention, particularly, a "preferred" embodiment, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein with the scope of this disclosure and the present invention and protected by the following claims.

Therefore, having thus described the invention, at least the following is claimed:

1. A method for using an internal pedicle insulator implant, comprising:
    inserting a pedicle screw in a pedicle;
    providing an internal pedicle insulator implant comprising a sheet having a first side for facing the pedicle screw and an opposing second side, the first side being shaped to complement an exterior shape of the pedicle screw;
    after inserting the pedicle screw in the pedicle, inserting the internal pedicle insulator implant into the pedicle such that the internal pedicle insulator implant is positioned between a nerve and the pedicle screw, with the first side of the internal pedicle insulator implant being positioned adjacent to the pedicle screw;
    applying material in the vicinity of the nerve through a fenestration in the pedicle screw such that the material is blocked from contacting the nerve by the internal pedicle insulator implant.

2. The method of claim 1, wherein the internal pedicle insulator implant has a substantially rectangular shaped peripheral edge.

3. The method of claim 1, further comprising:
    providing an internal pedicle insulator apparatus having:
        an outer insertion rod having an upper end and an opposing lower end; and
        an inner insertion rod having a top end and a bottom end, the inner insertion rod being axially slidably engaged inside the outer insertion rod;
    movably engaging the internal pedicle insulator implant with the inner insertion rod; and
    sliding the outer insertion rod along the inner insertion rod toward the internal pedicle insulator implant such that the internal pedicle insulator implant moves along the inner insertion rod.

4. The method of claim 1, wherein:
    the internal pedicle insulator implant is tubular, with the first side being an interior surface of the internal pedicle insulator implant and the second side being an exterior surface of the internal pedicle insulator implant; and
    in inserting the internal pedicle insulator implant, the internal pedicle insulator implant is inserted about the pedicle screw such that at least a portion of the pedicle screw extends into the interior of the implant.

5. The method of claim 4, wherein the internal pedicle insulator implant has a first anti-rotation fin protruding outwardly from the second surface.

6. The method of claim 1, wherein the internal pedicle insulator implant is curved about a longitudinal axis.

7. The method of claim 1, wherein the material is a biological substance.

* * * * *